United States Patent [19]

Erlanger et al.

[11] Patent Number: 5,925,532
[45] Date of Patent: *Jul. 20, 1999

[54] ENHANCING THE SENSITIVITY OF IMMUNOASSAY PROCEDURES BY USE OF ANTIBODIES DIRECTED TO THE PRODUCT OF A REACTION BETWEEN PROBE LABELS AND ASSAY SUBSTRATES

[75] Inventors: Bernard F. Erlanger, Whitestone; Bi-Xing Chen, New York, both of N.Y.

[73] Assignee: The Trustees of Columbia University in the City of New York, New York, N.Y.

[ * ] Notice: This patent is subject to a terminal disclaimer.

[21] Appl. No.: 08/898,583

[22] Filed: Jul. 22, 1997

Related U.S. Application Data

[63] Continuation-in-part of application No. PCT/US96/03549, Mar. 14, 1996, which is a continuation-in-part of application No. 08/403,649, Mar. 14, 1995, Pat. No. 5,650,284.

[51] Int. Cl.$^6$ .......................... G01N 33/53; G01N 33/542; G01N 33/543; G01N 33/537

[52] U.S. Cl. .......................... 435/7.9; 435/7.91; 435/7.71; 435/7.72; 435/7.92; 435/7.95; 435/5; 436/518

[58] Field of Search ..................................... 435/7.91, 7.9, 435/7.71, 7.72, 7.92, 7.95, 5; 436/518

[56] References Cited

U.S. PATENT DOCUMENTS

| | | |
|---|---|---|
| 4,446,231 | 5/1984 | Self . |
| 4,463,090 | 7/1984 | Harris . |
| 4,596,770 | 6/1986 | Parham et al. . |
| 4,684,609 | 8/1987 | Hsu . |
| 4,891,314 | 1/1990 | Pauly et al. . |
| 5,073,483 | 12/1991 | Lebacq . |
| 5,206,150 | 4/1993 | Tai et al. . |
| 5,238,817 | 8/1993 | Bobrow et al. . |
| 5,650,284 | 7/1997 | Erlanger et al. .......................... 435/7.1 |

OTHER PUBLICATIONS

Bobrow, M.N., et al. (1989) *J. Immuno. Methods* 125: 279–285;.
Bobrow, M.N., et al. (1991) *J. Immuno. Methods* 137: 103–112;.
Bobrow, M.N., et al. (1992) *J. Immuno. Methods* 150: 145–149;.
Cote, R.J., et al. (1983) *Proc. Natl. Acad. Sci., USA* 80: 2026–2030;.
Landsdorp, P.M., et al. (1984) *J. Histochem. Cytochem.* 32: 172–178;.
McKimm–Breschkin, J.L. (1990) *J. Immunol. Methods* 135: 277–280;.
Polack, J.M. and Van Noorden, S. (1983) *Immunocytochemistry: practical applications in pathology and biology* Wright, pp. 214–215;.
Spierto, F.W., et al. (1987) *J. Analytical Toxicology* 11: 31–35;.
Sternberger, L.A. (1986) *Immunocytochemistry*: Third Edition (Wiley and Sons;.
Chen, B.X., et al. (1996) *J. Histochem. Cytochem.* 44: 819–824;.
Hsu, S.M., et al. (1981) *Am. J. Clin. Pathol.* 75: 734–738;.
Avrameas, S. (1992) *J. Immunol. Methods* 150: 23–32.

*Primary Examiner*—Toni R. Scheiner
*Attorney, Agent, or Firm*—John P. White; Cooper & Dumham LLP

[57] ABSTRACT

The subject invention provides an antibody which specifically binds to the product of a reaction between a labeling substance and a substrate. The subject invention also provides a method of making an immunogen used to produce the antibody of the subject invention. The invention further provides methods of using the subject antibody for detecting an antigen of interest in a sample, for example, detecting a protein comprising an amino acid sequence of interest and detecting a nucleic acid molecule comprising a nucleic acid sequence of interest, detecting a polypeptide such as those expressed by infectious agents, fungi or parasites.

11 Claims, 8 Drawing Sheets

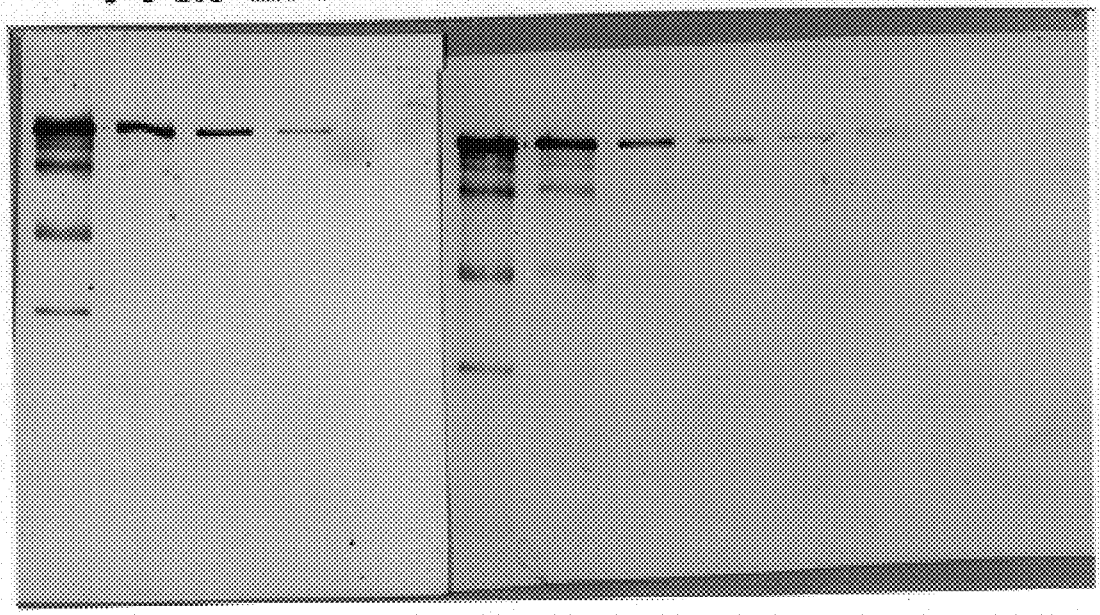

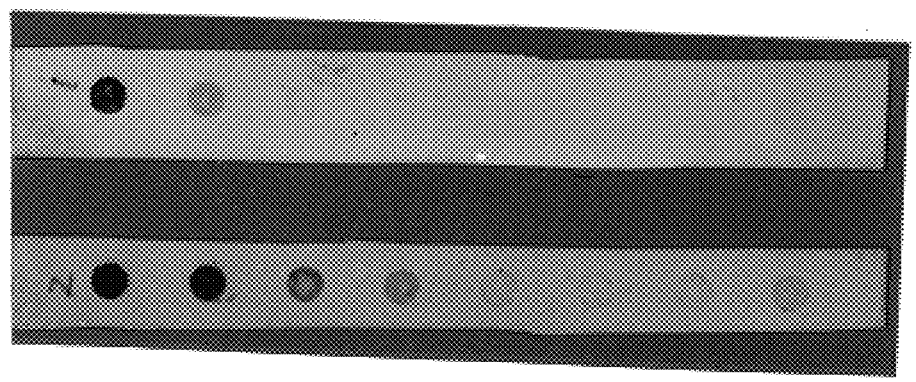

FIG. 5A
FIG. 5B
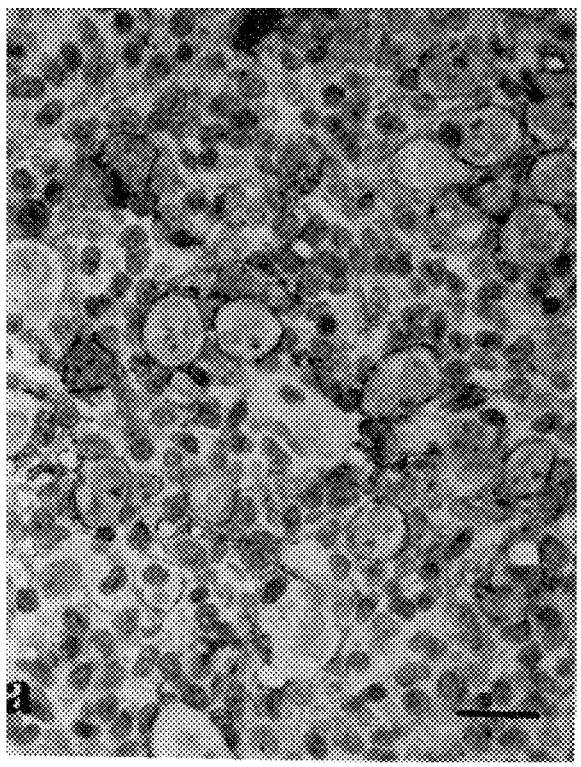 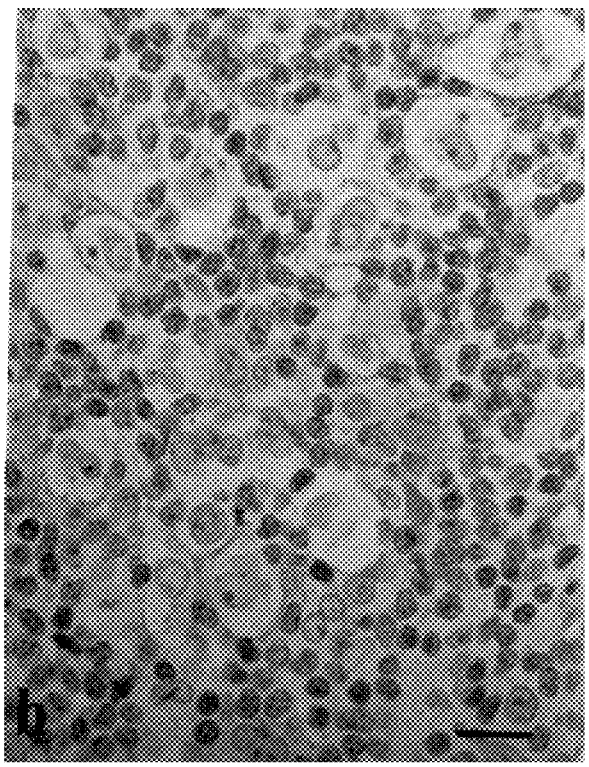

FIG. 5C
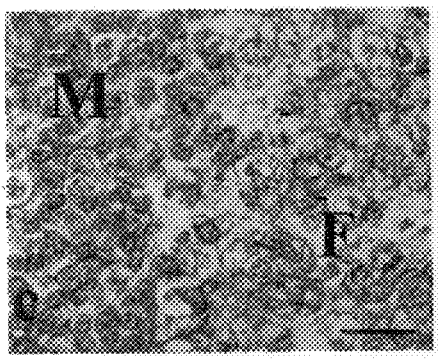
FIG. 5D
FIG. 5E
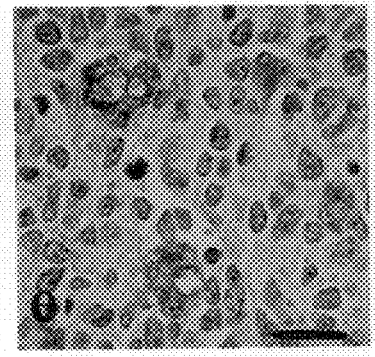
FIG. 5F
FIG. 5G
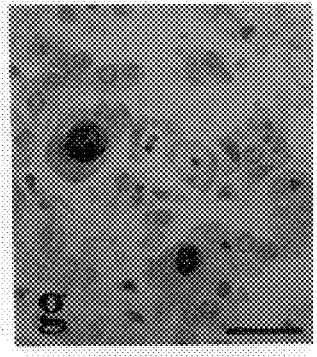
FIG. 5H

ENHANCING THE SENSITIVITY OF IMMUNOASSAY PROCEDURES BY USE OF ANTIBODIES DIRECTED TO THE PRODUCT OF A REACTION BETWEEN PROBE LABELS AND ASSAY SUBSTRATES

This application is a continuation-in-part of PCT International Application PCT/US96/03549, filed Mar. 14, 1996, which is a continuation-in-part of U.S. Ser. No. 08/403,649, filed Mar. 14, 1995, now U.S. Pat. No. 5,650,284.

The invention disclosed herein was made with Government support under Grant No. DE FG 02-88ER60742 from the U.S. Department of Energy. The U.S. Government has certain rights in this invention.

BACKGROUND OF THE INVENTION

Labeled antibodies are commonly used in immunoassays, such as ELISAs, in immunohistochemistry, and for identification of cellular components after gel electrophoresis such as the use of enzyme labeled antibodies in Western blot assays. The most common procedure is to detect the antigen with peroxidase-labeled specific antibody or first with unlabeled specific antibody followed with peroxidase-labeled anti-antibody. Addition of substrate, e.g., 3,3'-diaminobenzidine, results in a colored signal. In immunohistochemical experiments and in Western blots, the colored product is deposited at the site of the antigen. In cases in which the antigen is present at low levels, uncertain false negative results can be obtained. Accordingly, methods of amplifying the signal, without significant background "noise", have been sought.

Prior art immunoassays use peroxidase, frequently in the form of horseradish peroxidase, as a labeling enzyme coupled with a chromogen-hydrogen peroxide mixture as the substrate for detecting the antibodies. Further variations of the usual ELISA or EIA are disclosed in Sternberger, L. A., (1986) *Immunocytochemistry: Third Edition*, (Wiley and Sons); and Polak, J. M. and Van Noorden, S., (1983) *Immunocytochemistry: Practical Applications in Pathology and Biology*, Wright, pp. 214–215, wherein antibodies to peroxidase are used to detect peroxidase labeled antibodies bound to the molecule of interest. This method increases the specificity and sensitivity of the ELISAs.

Sternberger (1986) discloses that 3,3'-diaminobenzidine had been the preferred chromogen due to its high sensitivity and high insolubility, but was found to be carcinogenic and mutated samples. Further, McKimm-Breschkin, J. L., (1990) *J. Immunol. Methods*, Vol. 135, pages 277–280, discloses that although the preferred alternative has been 3,3',5,5'-tetramethylbenzidine (TMB), a non-mutagenic compound with similar properties, this compound when mixed with hydrogen peroxide in the reagent bottle breaks down, emitting color prematurely. Others, have disclosed that this premature reaction can be overcome by stabilizing the mixture with bacitracin, penicillin and N-methyl pyrrolidone. See U.S. Pat. No. 5,206,150, Tai, et al.; U.S. Pat. No. 4,891,314, Pauly, et al.; and U.S. Pat. No. 4,596,770, Parham, et al., the contents of which are hereby incorporated by reference.

The most widely used amplification procedure is through the use of peroxidase-labeled anti-peroxidase antibody, referred to as the "PAP" amplification. See, Sternberger, L. A., et al. (1970) *J. Histochem. Cytochem.*, Vol. 18, pages 315–333. Sternberger (1970) disclosed that the maximum amplification possible by the PAP procedure was approximately 12-fold. Further amplification is prevented by steric interference.

However, unlike PAP amplification, the subject invention provides the potential for exponential amplification. This is accomplished by the use of an antibody specific for the product of the label-substrate reaction. Because enzymes continuously "turn over" substrate molecules into product, reaction with the molecules of product produced by a single enzyme molecule can result in marked amplification of the signal, well beyond that seen by PAP amplification or other known techniques.

Because of the enhanced sensitivity of this method, the invention provides for low level detection and the reduction of the occurrence of false negatives in all types of immunohistochemical detection. The invention further allows for the use of smaller amounts of antibodies directed to a target antigen, which antibodies may be in short supply or may be prohibitively expensive. The invention further provides an alternative to PCR detection of nucleic acids. These and other uses are more fully described below. Further uses apparent to those of ordinary skill in the art based on this description of the invention are deemed within the scope of the invention.

SUMMARY OF THE INVENTION

This invention provides an antibody which specifically binds to the product of a reaction between a labeling substance and a substrate.

The subject invention also provides a method of detecting an antigen of interest in a sample which comprises (a) contacting the sample suspected of containing the antigen with a first labeled antibody which specifically binds the antigen under appropriate conditions to form a complex comprising the first labeled antibody bound to the antigen; (b) removing any labeled antibody not bound in the complex formed; (c) contacting the resulting complex from (b) with a substrate under appropriate conditions to produce a product of a reaction between the substrate and the labeling substance of the first labeled antibody in the complex of (b); (d) contacting the product produced in (c) with a second labeled antibody which specifically binds the product under appropriate conditions to permit the second labeled antibody to bind to the product; (e) removing any second labeled antibody not bound to the product in (d); and (f) detecting the bound second labeled antibody, thereby detecting the antigen of interest.

It should be noted that the sensitivity of the method may be further enhanced by repeating steps (c)–(f) using the product of the previous cycle as the complex from step (b). The cycle may theoretically be repeated infinitely many times but, as the enhancement is increased exponentially for each cycle, only several cycles are likely necessary for adequate detection of an antigen.

Additionally, it should be noted that the invention alternatively contemplates that the first antibody is not labeled but, following step (b), the first (unlabeled) antibody is contacted with a labeled anti-species antibody which specifically binds to the first antibody under appropriate conditions to form a complex comprising the anti-species antibody bound to the first antibody bound to the antigen. Subsequently, any labeled anti-species antibody not bound in the complex formed is removed and the complex is treated in the same way as the complex of step (b) above.

The subject invention also provides a method for detecting a protein comprising an amino acid sequence of interest in a sample which comprises (a) contacting the sample suspected of containing the protein comprising the amino acid sequence of interest with a first labeled antibody which specifically binds the amino acid sequence of interest under appropriate conditions to produce a complex comprising the first labeled antibody bound to any protein comprising the amino acid sequence of interest in the sample; (b) removing any labeled antibody not bound in the complex formed in step (a); (c) contacting the complex of (b) with a substrate under appropriate conditions to produce a product of a reaction between the substrate and the labeling substance of the first labeled antibody in the complex of (b); (d) contacting the product produced in (c) with a second labeled antibody which specifically binds the product under appropriate conditions to permit the second labeled antibody to bind to the product; (e) removing any second labeled antibody not bound to the product in (d); and (f) detecting the bound second labeled antibody, thereby detecting the protein.

The subject invention further provides a method of making an immunogen to be used to make an antibody directed to the product of a reaction between a substrate and a labeling substance which comprises (a) combining a labeling substance with a substrate under appropriate conditions to produce a reaction between the labeling substance and the substrate; (b) quenching the reaction of step (a) at a point in time where an intermediate of the reaction product is formed; (c) isolating the intermediate; and (d) combining the intermediate with a carrier molecule under appropriate conditions to allow the intermediate to bind to the carrier molecule, thereby forming the immunogen. The subject invention further provides an immunogen made by this method The subject invention provides a method of producing an antibody which specifically binds to the product of a reaction between a substrate and a labeling substance which comprises immunizing an animal with the immunogen and recovering the antibody produced by the animal.

The subject invention provides a method of producing a monoclonal antibody directed to the product of a reaction between a substrate and a labeling substance which comprises immunizing a mouse with the immunogen of this invention, extracting the antibody-producing lymphocytes from the spleen of the mouse, fusing the lymphocytes with an immortal cell line to form a hybridoma cell, selecting the hybridoma cells which produce the antibody, and recovering the antibody from the hybridoma cells.

Finally, the subject invention provides a method for detecting a nucleic acid molecule comprising a nucleic acid sequence of interest in a sample which comprises (a) contacting the sample suspected of containing the nucleic acid molecule comprising the nucleic acid sequence of interest with a labeled probe, wherein the probe comprises a nucleic acid molecule having a nucleic acid sequence complementary to the nucleic acid sequence of interest under appropriate conditions to produce a complex comprising the labeled probe bound to any nucleic acid molecule comprising the nucleic acid sequence of interest in the sample; (b) removing any labeled probe not bound in the complex of (a); (c) contacting the complex from (b) with a substrate under appropriate conditions to produce a product of a reaction between the substrate and the labeling substance of the labeled probe bound to the complex from (b); (d) contacting the product produced in (c) with a labeled antibody which specifically binds the product under appropriate conditions to permit the antibody to bind to the product; and (e) detecting the labeled antibody, thereby detecting the antigen of interest.

1A. Detection CsA-BBA-BSA conjugate by peroxidase labeled anti-mouse IgG antibody and 3,3'-diaminobenzidine.

1B. Detection method of 1A amplified by PAP amplification technique.

1C and 1D. Detection method of 1A using amplification technique of claimed invention employing purified antibody (1C) and unpurified antiserum (1D).

FIGS. 2A and 2B: Western blot of mouse immunoglobulin G protein electrophoresed in SDS-polyacrylamide gel. Development of blot using standard peroxidase labeled goat anti-mouse IgG antibody and 3,3'-diaminobenzidine (2A) and using amplification technique of claimed invention (2B).

FIGS. 3A and 3B: Detection of DNA molecule by dot blot. Development of blot using standard peroxidase labeled goat anti-mouse IgG antibody and 3,3'-diaminobenzidine (3A) and using amplification technique of claimed invention (3B).

Figure 4:
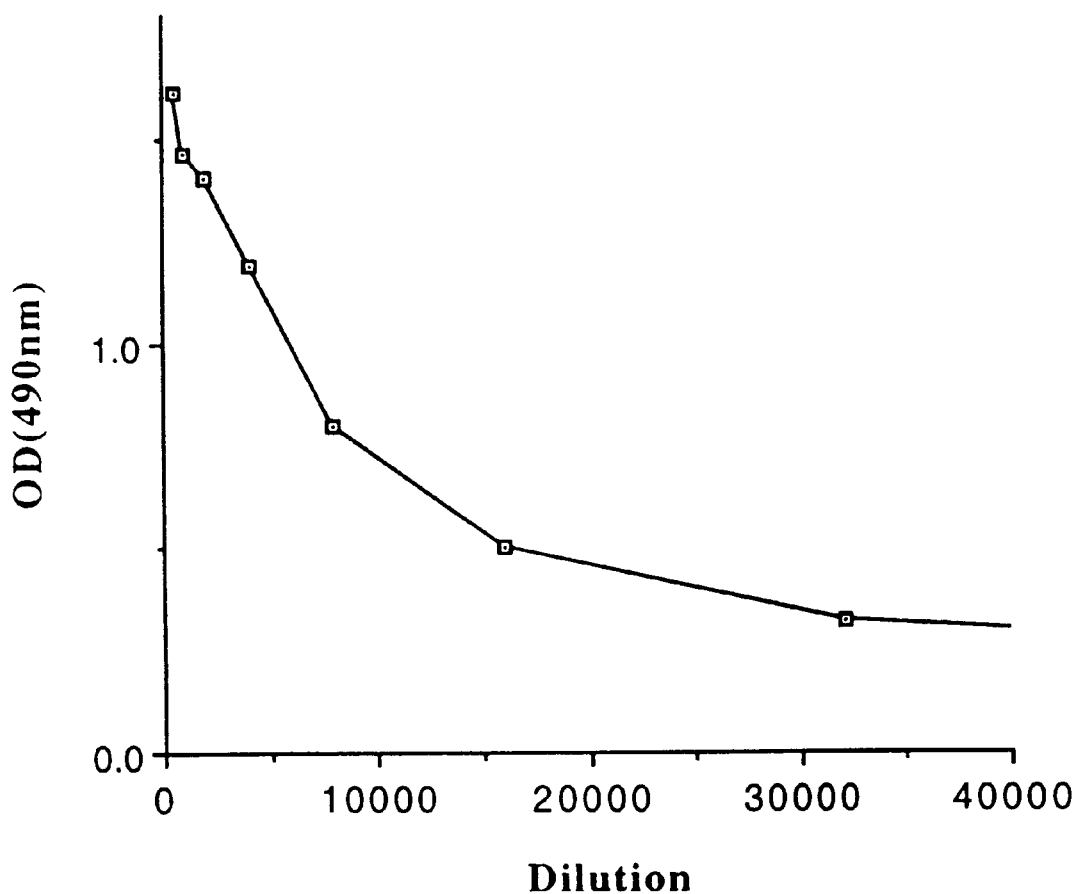
Figure 6A:
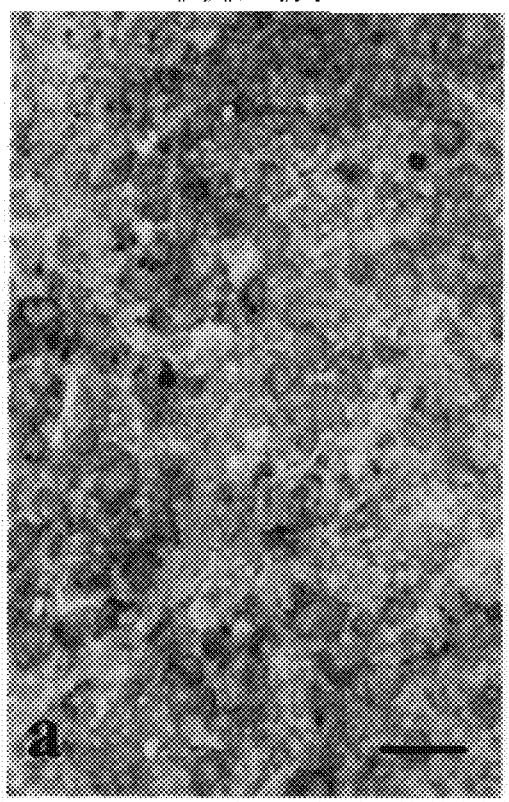
Figure 6B:
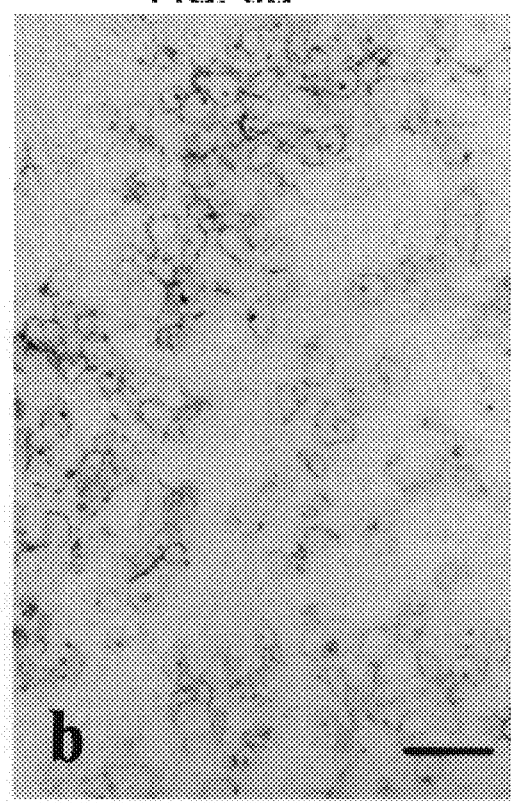
Figure 6C:
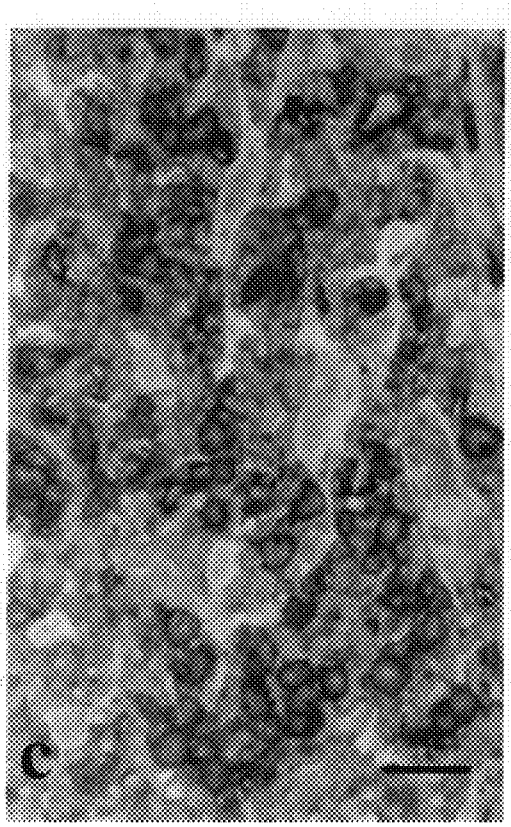
Figure 6D:
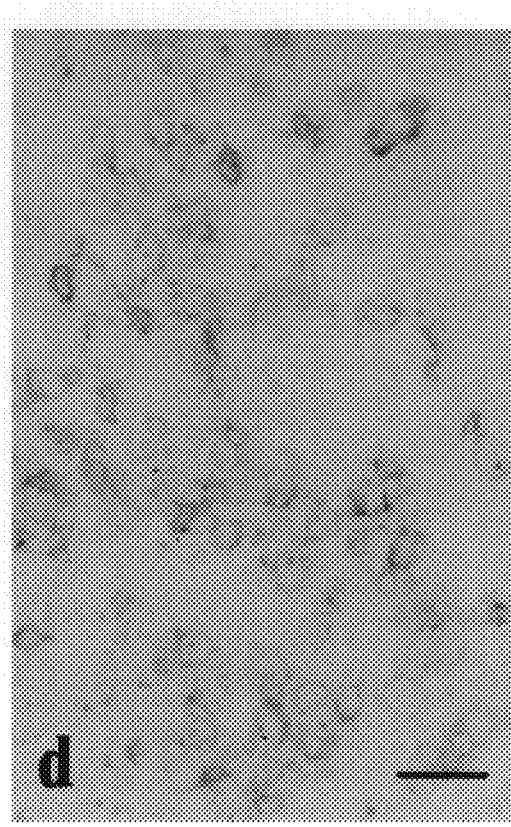
Figure 6E:
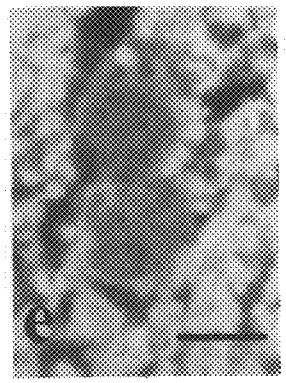
Figure 6F:
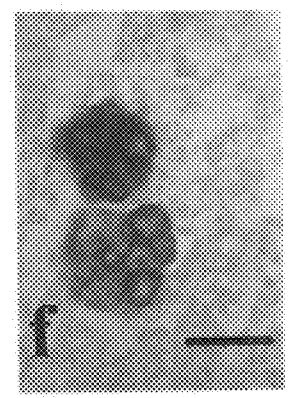
Figure 6G:
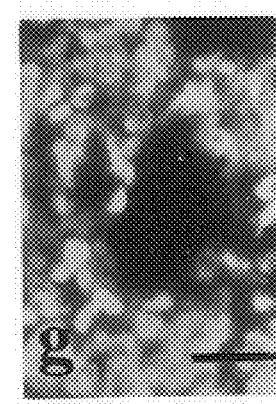
Figure 6H:
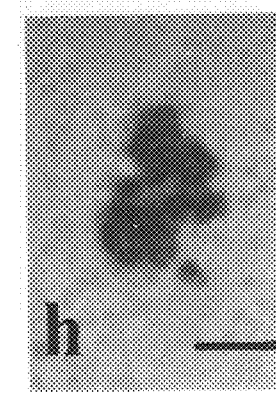

FIG. 4: Titration of the anti-EP antibody by ELISA. Corning 96-well plates wre coated with the RSA conjugate of DAB polymerized by the controlled reaction of horseradish peroxidase and $H_2O_2$. Development was with a peroxidase-labeled goat anti-rabbit Ig. Details are given in Materials and Methods.

FIGS. 5A–5H: Immunolabeling of Hodgkin's disease (5A and 5B), a hyperplastic tonsil (5C–5F) and a case of CMV pneumonia (5G and 5H) with antisera to CD30 (1:800) (5A, SB) CD20 (1:3200) (5C and 5D), CD68 (5E and 5F), and CMV (1:200) (5G and 5H). The signal in EP-amplified setions (5A, 5C, 5E, 5G) is much stronger than in the unamplified control section stained with the conventional avidinbiotin technique (5B, 5D, 5f, 5H), when equal dilutions of the primary Ab were used. The numbers of CD 30-immunoreactive Reed-Sternberg cells (5A and 5B), CD20-positive B-lymphocytes (5C and 5D), both in the mantle zone (M) and the follicular center (f) of tonsil lymph follicles, CD68-reactive macrophages (5E and 5F), and CMV-infected alveolocytes are also increased in EP-amplified (5A, 5C, 5E and 5G) versus unamplified (5B, 5D, 5F and 5H) sections. Original magnifications ×400. Bars=20 μm.

FIGS. 6A–6H: Immunostaining of Reed-Sternberg cells in a case of Hodgkin's disease with anti-CD30 (6A–6D) an a toxoplasmosis cyst in the brain with anti-toxoplasma Ab (6E–6H). The presence of anti-EP Ab is visualized by red fluorescence (6A and 6E) which corresponds exactly to the distribution of DAB (6B and 6F) representing binding of the primary Ab. Omission of the anti-EP Ab (6C, 6D, 6G, 6F) was used as a negative control. The yellow-green autofluorescence in 6C and 6G is quenched by the deposition of DAB, demonstrated in 6D and 6H. Original magnifications: 6A–6D×250; 6E–6H ×400. Bars: 6A–6D=30 μm; 6E–6H= 20 μm.

DETAILED DESCRIPTION

The subject invention provides an antibody which specifically binds to the product of a reaction between a labeling substance and a substrate.

The term "antibody" as used herein refers to both polyclonal and monoclonal antibodies. In addition, the term includes whole monoclonal antibodies as well as antigen binding fragments thereof. Examples of such fragments are well known to those of ordinary skill in the art and are referred to as Fab, Fab' or F(ab')$_2$ antibody fragments. In a preferred embodiment the monoclonal antibody fragment is a Fab' fragment. In another preferred embodiment the monoclonal antibody fragment is a F(ab')$_2$ fragment. Methods of producing the antibody fragments are also known to those of ordinary skill in the art. By way of example, the Fab' fragment of the above-disclosed monoclonal antibody can be produced by papain digestion of the monoclonal antibody. Similarly, the F(ab')$_2$ fragment can be produced by pepsin digestion of the monoclonal antibody.

Methods of making the claimed antibodies, both polyclonal and monoclonal, are more fully described below. The polyclonal antibody of this invention can be unpurified polyclonal antiserum or a purified polyclonal antibody. Techniques for purifying antibodies are well known to those of ordinary skill in the art and include, but are not limited to, techniques employing hydroxyapatite, gel filtration, ammonium sulfate/DEAE, caprylic acid/ammonium sulfate, protein A beads, antigen affinity columns and anti-Ig affinity columns. Methods employing these techniques are discussed in Harlow & Lane, *Antibodies: A Laboratory Manual*, (Cold Spring Harbor Laboratories, Cold Spring Harbor, N.Y.: 1988) the contents of which are hereby incorporated by reference.

The term "labeling substance" as used herein refers to any substance which can used to label compositions of matter, such as antibodies or probes, which allows for the detection of the composition of matter. Examples of labeling substances are well known to those of ordinary skill in the art and include, but are not limited to, such substances as enzymes, dyes, fluorescent markers, radioactive isotopes or biotin.

The term "substrate" as used herein refers to any substance which can be used to resolve a labeling substance. For example, in standard immunoassays detection of the target is accomplished by detection of the labeling substance when elucidated by reaction with a substrate. A "reaction", as used herein, takes place when the labeling substance and substrate combine to form a product which can be detected. Detection can be visual or mechanical. Visual detection usually involves detection of a precipitate or other product which changes the color of the reaction medium. Mechanical detection can be detection of any product formed by the reaction such as detection of any changes the color of the reaction medium, or detection of other "products" such as detection of radiation of heat, light or radioactive waves.

The subject invention therefore contemplates the use of any labeling substance and any substrate which, when reacted with each other, form a product which can then be administered to an animal, which animal will produce an antibody directed against the product. The antibody of the subject invention, which is an antibody which specifically binds the product, is therefore useful for detecting the product when the product is present in an assay as the result of the reaction between the labeling substance and substrate in the assay. The above-described antibody therefore allows for exponential amplification of normal assay techniques by permitting indirect detection of a labeled target through direct detection of the product of the reaction between the labeling substance bound to the target and substrate added to the assay. The antibody of the invention detects this product which is more abundant than the bound label because of the ongoing reaction between the label and substrate.

In a preferred embodiment of the subject invention the labeling substance is an enzyme. Enzymes useful in the practice of the invention include peroxidase, such as horseradish peroxidase, or other enzymes such as alkaline phosphatase and β-galactosidase.

When the labeling substance is an enzyme a preferred embodiment of the substrate is benzidine or a derivative of benzidine. Derivatives of benzidine include substituted derivatives containing one or more alkyl, aryl, amino, bromo, chloro, fluoro or iodo substituents. Examples include but are not limited to 3,3'-diaminobenzidine, 3,3',5,5',-tetramethylbenzidine. The subject invention also contemplates the addition of metal salts such as cobalt or nickel when benzidine or benzidine derivatives are used as the substrate to enhance the formation of the reaction product. Other substrates useful for the practice of the subject invention include derivatives of the compounds carbazole and naphthol such as derivatives which contain one or more alkyl, aryl, amino, bromo, chloro, fluoro or iodo substituents. Examples include, but are not limited to, 3-amino-9-ethyl carbazole and 4-chloro-1-naphthol. The subject invention also contemplates the use of other substrates known by those of ordinary skill in the art such as nitrophenylphosphate, bromochloroindolyl-nitro blue tetrazolium, naphthol-AS-BI-phosphate/new fuchsin and bromochloroindolyl-β-galactopyranoside. A particular example of a suitable substrate used when the enzyme is alkaline phosphatase is nitro blue tetrazolium chloride whose formal name is (2,2'-di-p-nitrophenyl-5,5'-diphenyl-3,3'-[3,3'-dimethoxy-4,4'-diphenylene])-ditetrazolium chloride. The product of alkaline phosphatase and nitro blue tetrazolium chloride is a formazan, for which we have made the antibody. Other related tetrazolium derivatives would be expected to react similarly to make formazans. Any similar enzyme/substrate combination which produces a reaction product as defined above would therefore be useful in the practice of the subject invention.

The detection of the antibodies of the subject invention provides the amplification of the standard assay. Such detection can be accomplished by standard techniques. For example, the antibodies of the subject invention, either polyclonal or monoclonal, can be labeled with a detectable label. The detectable labels useful in the practice of this invention include such substances as enzymes, dyes, fluorescent markers, colored beads, radioactive isotopes or biotin. In a preferred embodiment the antibody of the subject invention can be labeled with a coenzyme such as biotin using the process of biotinylation. When biotin is used as a label, the detection of the antibody is accomplished by addition of a protein such as avidin or its bacterial counterpart streptavidin, either of which can be bound to a detectable marker such as the aforementioned dye, a fluorescent marker such as fluorescein, a colored bead, a radioactive isotope or an enzyme such as peroxidase.

The antibodies of the subject invention can also be detected by use of another antibody which specifically bind the antibodies of the subject invention. Such antibodies can further be labeled for detection by known methods as detailed above. Methods for producing such anti-antibodies are known to those of ordinary skill in the art such as those disclosed in Harlow & Lane, *Antibodies: A Laboratory Manual*, cited above.

The subject invention also provides a method of detecting an antigen of interest in a sample which comprises:
  a) contacting the sample suspected of containing the antigen with a first labeled antibody which specifically binds the antigen under appropriate conditions to form a complex comprising the first labeled antibody bound to the antigen;

b) removing any labeled antibody not bound in the complex formed in (a);

c) contacting the resulting complex from (b) with a substrate under appropriate conditions to produce a product of a reaction between the substrate and the labeling substance of the first labeled antibody in the complex of (b);

d) contacting the product produced in (c) with a second labeled antibody which specifically binds the product under appropriate conditions to permit the second labeled antibody to bind to the product;

e) removing any second labeled antibody not bound to the product in (d); and f) detecting the bound second labeled antibody, thereby detecting the antigen of interest.

In the practice of this method, the conditions of the "contacting" in step (a) permitting the first labeled antibody to form a complex with the antigen comprise incubation of a culture of the antibody and the sample suspected containing the antigen of interest. Incubation can be carried out at a temperature range of from about 4° C. to about 37° C. for a period of from about on half hour to 3 hours. In the preferred embodiment the incubation is carried out at 37° C. for 1 hour.

The separations in steps (b) and (e) of unbound antibody from bound antibody can be carried out by any method known to those skilled in the art. An example of such methods include precipitation of the complex with an anti-mouse globulin.

The "contacting" in step (c) permitting the formation of a product of the reaction between a substrate and the labeling substance of the first labeled antibody comprises the addition of the substrate to the culture containing the bound first labeled antibody and reacting the substrate with the labeled antibody at approximately room temperature for a period of approximately 15 minutes to one hour.

The conditions of the "contacting" in step (d) permitting the second labeled antibody to form a complex with the product of the reaction between the labeling substance and the substrate comprise further incubation of the complex from step (c). Incubation can be carried out at a temperature range of from about 4° C. to about 37° C. for a period of from about on half hour to 3 hours. In the preferred embodiment the incubation is carried out at 37° C. for 1 hour.

In a preferred embodiment of the above method, the first labeled antibody is labeled with an enzyme such as peroxidase, alkaline phosphatase or β-galactosidase.

In a preferred embodiment wherein the labeled antibody is labeled with an enzyme the preferred substrate is benzidine or a derivative of benzidine as detailed above.

In a particularly preferred embodiment of the above method the derivatives of benzidine include 3,3'-diaminobenzidine or 3,3',5,5'-tetramethylbenzidine.

In the practice of the invention the second labeled antibody can be labeled with an enzyme, dye, fluorescent marker, colored bead or radioactive isotope. The second labeled antibody is then detected using techniques known to those of ordinary skill in the art as described above.

In a preferred embodiment of the subject invention, the above described method is used to detect cell-associated and/or tissue-associated antigens. Those of ordinary skill in the art will recognize that many references exist detailing the production of antibodies to cell- and tissue-associated antigens. For example, see such patents as U.S. Pat. No. 5,354,847, issued Oct. 11, 1994 to Liu et al. concerning monoclonal antibodies to human tumor antigen L6 and U.S. Pat. No. 5,348,880, issued Sep. 20, 1994 to Hanna, Jr. et al. concerning monoclonal antibodies to human B-cell tumor antigen. More generally, see R. J. Cote et al. "Generation of Human Monoclonal Antibodies Reactive with Cellular Antigens," *Proc. Nat. Acad. Sci.*, Vol. 80, (April 1983) pages 2026–2030. These publications and the references cited therein are hereby incorporated in their entirety into the subject application. These antibodies are useful for screening for, and therapy of, abnormalities of the tissues or cells to which the antigens are associated.

In the practice of the subject invention, such known antibodies represent a "first antibody", used for the detection of the antigen of interest. The antibodies of the subject invention represent the "second antibody" and in the above-described method, are used to detect the "first antibody." The methods of the subject invention provide the route to detect any antigen of interest by amplifying the detection of any such "first antibody" labeled with a substance which forms a detectable product upon reaction with a substrate as described above. Therefore, any tissue- and cell-associated antigens known to those of ordinary skill in the art, or those yet to be made, which can be labeled with detectable markers are useful in the practice of the subject invention and are considered to be within the scope of the present invention.

As used herein "antigen" means any substance capable of binding to the first antibody of step (a) in the above-described methods and includes polypeptides and non-peptidyl compounds.

As used herein "non-peptidyl compounds" mean compounds that are not peptides. For example, a non-peptidyl compound is cholesterol, hormones or other non-peptide based compounds.

Polypeptides include, but should not be limited to, naturally occurring proteins, recombinant proteins, mutants, and fragments thereof.

As used herein "mutants," include, but are not limited to, polypeptides differing from naturally occurring proteins by one base pair, e.g. deletion, insertion or substitution. Further, for example, using this method, one could detect polypeptides produced by the translocation of genomic DNA encoding a naturally occurring protein. A further embodiment of this invention is its use in detecting aberrant levels of expression of proteins, e.g. overexpression or low levels of expression.

In a specific embodiment of this method the target antigen can be any cell-associated antigen or tissue-associated antigen. Examples of cell-associated antigens include cells of plants or animals. Examples of animal cells possessing antigens against which the subject invention would be useful include, but are not limited to, blood cells, tumor cells and fat cells. In a particularly preferred embodiment the method is useful against antigens associated with malignant cells including but not limited to such cells as leukemic cells.

Examples of tissues against which the subject invention would be useful include such animal tissue as bone, skin, muscle and internal organs, including but not limited to brain, heart, lung, stomach, liver, pancreas and intestine. In a preferred embodiment the tissue-associated antigen is a tumor-associated antigen in a tissue comprising the tumor. As used herein "tumor" means any abnormal mass of tissue that arises from cells of preexistent tissue. Such tumors can be those characterized as benign or malignant tumors, such as cancerous tumors. Examples include, but are not limited to, tumors of the brain, central nervous system, mouth, throat, lung, breast, ovary, testes, colon, stomach, bone, skin, pancreas, bladder, cervix, thyroid or prostate. The above described method is also useful against antigens associated with lymphomas.

In another specific embodiment of this method, the antigen can be a polypeptide expressed by an infectious agent. Examples of infectious agents include, but are not limited to, viruses, bacteria, protozoa, and microorganisms. Specifically, the virus may be a cytomegalovirus. In another specific embodiment, the microorganism is a mycoplasma.

Further, the polypeptide may be expressed by a fungus or a parasite.

The subject invention also provides a method for detecting a protein comprising an amino acid sequence of interest in a sample which comprises:

a) contacting the sample suspected of containing the protein comprising the amino acid sequence of interest with a first labeled antibody which specifically binds the amino acid sequence of interest under appropriate conditions to produce a complex comprising the first labeled antibody bound to any protein comprising the amino acid sequence of interest in the sample;

b) removing any labeled antibody not bound in the complex formed in step (a);

c) contacting the complex of (b) with a substrate under appropriate conditions to produce a product of a reaction between the substrate and the labeling substance of the first labeled antibody in the complex of (b);

d) contacting the product produced in (c) with a second labeled antibody which specifically binds the product under appropriate conditions to permit the second labeled antibody to bind to the product;

e) removing any second labeled antibody not bound to the product in (d); and f) detecting the bound second labeled antibody, thereby detecting the protein.

In the practice of this method, the conditions of the "contacting" in step (a) permitting the first labeled antibody to form a complex with the protein of interest in a sample comprise incubation of a culture of the antibody and the sample suspected containing the protein of interest. Incubation can be carried out at a temperature range of from about 4° C. to about 37° C. for a period of from about on half hour to 3 hours. In the preferred embodiment the incubation is carried out at 37° C. for 1 hour.

The separations in steps (b) and (e) of unbound antibody from bound antibody can be carried out by any method known to those skilled in the art. An example of such methods include precipitation of the complex with an anti-mouse globulin.

The "contacting" in step (c) permitting the formation of a product of the reaction between a substrate and the labeling substance of the first labeled antibody comprises the addition of the substrate to the culture containing the bound first labeled antibody and reacting the substrate with the labeled antibody at approximately room temperature for a period of approximately 15 minutes to one hour.

The conditions of the "contacting" in step (d) permitting the second labeled antibody to form a complex with the product of the reaction between the labeling substance and the substrate comprise further incubation of the complex from step (c). Incubation can be carried out at a temperature range of from about 4° C. to about 37° C. for a period of from about on half hour to 3 hours. In the preferred embodiment the incubation is carried out at 37° C. for 1 hour.

In a preferred embodiment of the above method, the first labeled antibody is labeled with an enzyme such as peroxidase, alkaline phosphatase or β-galactosidase.

In a preferred embodiment wherein the labeled antibody is labeled with an enzyme the preferred substrate is benzidine or a derivative of benzidine as detailed above.

In a particularly preferred embodiment of the above method the derivatives of benzidine include 3,3'-diaminobenzidine or 3,3',5,5'-tetramethylbenzidine.

In the practice of the invention the second labeled antibody can be labeled with an enzyme, dye, fluorescent marker, colored bead or radioactive isotope. The second labeled antibody is then detected using techniques known to those of ordinary skill in the art as described above.

In a separate embodiment, the above method of detecting a protein can also be used to detect a polysaccharide. In such an embodiment the first labeled antibody would be an antibody which specifically binds to any sugar moiety of which the polysaccharide is comprised.

The subject invention further provides method of making an immunogen to be used to make an antibody directed to the product of a reaction between a substrate and a labeling substance which comprises:

a) combining a labeling substance with a substrate under appropriate conditions to produce a reaction between the labeling substance and the substrate;

b) quenching the reaction of step (a) at a point in time where an intermediate of the reaction product is formed;

c) isolating the intermediate; and d) combining the intermediate with a carrier molecule under appropriate conditions to allow the intermediate to bind to the carrier molecule, thereby forming the immunogen.

In the practice of the above method any labeling substance and any substrate which can be combined to form a product for detection can be used. "Combining" can consist of forming a solution of the two reaction products. For example, peroxidase and benzidine or a derivative of benzidine can be combined to produce a product. The solution can be formed by dissolving the benzidine or derivative in phosphate buffered saline (PBS) and then adding peroxidase in distilled water. The labeling substance and substrate are combined in molar ratio of between 1:20 to 1:50 labeling substance to substrate. The reaction can be carried out for a period of between 2–8 hours at a temperature range of between 4° C. and 36° C. Alternatively the reaction can be allowed to proceed overnight at a temperature of approximately 4° C. The reaction progress is analyzed for a point in time when an intermediate begins to form such as by detection of the appearance of, or change in, color in the solution. When benzidine and peroxidase are used, color appears instantly and becomes bright red. At this time the reaction is quenched, for example, by the addition of a spatular tip of palladium black. Other methods of quenching reactions are well known to those of ordinary skill in the art. These are equally applicable in the above described method and contemplated within the scope of the subject invention.

Following the quenching of the reaction the product is isolated by centrifugation. The reaction product in the supernatant is then combined with the carrier molecule to form the immunogen used to immunize the animals. Carrier molecules useful in the practice of the subject invention comprise any macromolecule which can be bound to the above described product to provide a vehicle for administering the product to an animal as an immunogen in order to illicit an immune response in the animal which thereby produces antibodies specific for the product. Examples of useful macromolecule include but are not limited to polysaccharides, complex carbohydrates, and any organic polymer including polyacrylamide, polynitrocellulose and polystyrene. In a preferred embodiment of this invention the carrier molecule is a polypeptide. In a particularly preferred embodiment the polypeptide is a protein. Proteins useful as carrier molecules include but are not limited to bovine serum albumin, rabbit serum albumin, keyhole limpet hemocyanin, ovalbumin or any globulin such as thyroglobulin.

The carrier molecule is combined with the product according to known methods. For example, a solution of the protein bovine serum albumin (BSA) in PBS can be prepared and the product combined with the BSA solution to form the immunogen which comprises the product bound to the carrier molecule. The product and carrier molecule are reacted at a molar ratio of between approximately 1:2 and 1:5. The reaction can proceed at room temperature for a period of approximately 6 to 12 hours.

The subject invention further provides the immunogen made by this method.

The subject invention also provides a method of producing an antibody which specifically binds to the product of a reaction between a substrate and a labeling substance which comprises immunizing an animal with the above-described immunogen and recovering the antibody produced by the animal.

Polyclonal antibodies may be produced by injecting a host animal such as rabbit, rat, goat, mouse or other animal with the immunogen of this invention. The sera are extracted from the host animal and are screened to obtain polyclonal antibodies which are specific to the immunogen. Methods of screening for polyclonal antibodies are well known to those of ordinary skill in the art such as those disclosed in Harlow & Lane, *Antibodies: A Laboratory Manual*, cited above.

In a preferred embodiment of the above described method wherein in the animal is a rabbit, mouse or goat.

This invention also provides a method of producing a monoclonal antibody directed to the product of a reaction between a substrate and a labeling substance which comprises immunizing a mouse with the above describe immunogen, extracting the antibody-producing lymphocytes from the spleen of the mouse, fusing the lymphocytes with an immortal cell line to form a hybridoma cell, selecting the hybridoma cells which produce the antibody, and recovering the antibody from the hybridoma cells.

The monoclonal antibodies may be produced by immunizing for example, mice with an immunogen. The mice are inoculated intraperitoneally with an immunogenic amount of the above-described immunogen and then boosted with similar amounts of the immunogen. Spleens are collected from the immunized mice a few days after the final boost and a cell suspension is prepared from the spleens for use in the fusion.

Hybridomas may be prepared from the splenocytes and a murine tumor partner using the general somatic cell hybridization technique of Kohler, B. and Milstein, C., *Nature* (1975) 256: 495–497. Available murine myeloma lines, such as those from the American Type Culture Collection (ATCC) 12301 Parklawn Drive, Rockville, Md. 20852 USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas may be expanded, if desired, and supernatants may be assayed by conventional immunoassay procedures, for example, radioimmunoassay, using the immunizing agent as antigen. Positive clones may be characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

The subject invention also provides the antibodies, either polyclonal or monoclonal, produced by the above-described methods. These antibodies can also be labeled with a detectable label. The detectable labels useful in the practice of this invention include such substances as enzymes, dyes, fluorescent markers, colored beads, radioactive isotopes or biotin.

Finally, the subject invention provides a method for detecting a nucleic acid molecule comprising a nucleic acid sequence of interest in a sample which comprises:

a) contacting the sample suspected of containing the nucleic acid molecule comprising the nucleic acid sequence of interest with a labeled probe, wherein the probe comprises a nucleic acid molecule having a nucleic acid sequence complementary to the nucleic acid sequence of interest under appropriate conditions to produce a complex comprising the labeled probe bound to any nucleic acid molecule comprising the nucleic acid sequence of interest in the sample;

b) removing any labeled probe not bound in the complex of (a);

c) contacting the complex from (b) with a substrate under appropriate conditions to produce a product of a reaction between the substrate and the labeling substance of the labeled probe bound to the complex from (b);

d) contacting the product produced in (c) with a labeled antibody which specifically binds the product under appropriate conditions to permit the antibody to bind to the product; and e) detecting the labeled antibody, thereby detecting the antigen of interest.

In the practice of this method, the conditions of the "contacting" in step (a) permitting the first labeled antibody to form a complex with the nucleic acid molecule of interest in a sample comprise incubation of a culture of the antibody and the sample suspected containing the nucleic acid molecule of interest. Incubation can be carried out at a temperature range of from about 4° C. to about 37° C. for a period of from about one half hour to 3 hours. In the preferred embodiment the incubation is carried out at 37° C. for 1 hour.

The separation in step (b) of unbound probe from bound probe can be carried out by any method known to those skilled in the art.

The "contacting" in step (c) permitting the formation of a product of the reaction between a substrate and the labeling substance of the first labeled antibody comprises the addition of the substrate to the culture containing the bound first labeled antibody and reacting the substrate with the labeled antibody at approximately room temperature period of from about 10 minutes to one hour.

The conditions of the "contacting" in step (d) permitting the labeled antibody to form a complex with the product of the reaction between the labeling substance and the substrate comprise further incubation of the complex from step (c). Incubation can be carried out at a temperature range of from about 4° C. to about 37° C. for a period of from about on half hour to 3 hours. In the preferred embodiment the incubation is carried out at 37° C. for 1 hour.

In a preferred embodiment of the above described method the labeled probe is labeled with an enzyme such as peroxidase, alkaline phosphatase or β-galactosidase.

The term "probe" as used herein refers to any nucleic acid molecule which can be labeled and which forms a double helix by binding with a molecule containing a nucleic acid sequence of interest through complementary base paring. Those skilled in the art also refer to such probes as "hybridization probes". For example, when using a DNA probe to locate a DNA sequence of interest, a sample containing double stranded DNA can be reacted with the DNA probe to locate any DNA molecule in a sample which comprises the sequence of interest ("target DNA"). In such methods, the double stranded DNA in the sample is disassociated into its single strands and then reacted with a DNA probe. The probe binds to any target DNA in the sample by complementary base paring, i.e., adenine matches with thymidine and guanine with cytosine. The DNA probe, therefore, is a single strand of a DNA double helix which comprises nucleic acid molecules which are complementary to the sequence of interest.

Methods of making labeled nucleic acid probes, both DNA and RNA, are well known to those of ordinary skill in the art. The above described method therefore allows for the amplification of the detection of a nucleic acid molecule of interest which may be present in small amounts in a sample yet be undetectable.

In a preferred embodiment the labeled probe is labeled with an enzyme the preferred substrate is benzidine or a derivative of benzidine as detailed above. In a particularly preferred embodiment of the above method the derivatives of benzidine include 3,3'-diaminobenzidine or 3,3',5,5'-tetramethylbenzidine.

In the practice of the invention the labeled antibody can be labeled with an enzyme, dye, fluorescent marker, colored bead or radioactive isotope. The labeled antibody is then detected using techniques known to those of ordinary skill in the art as described above.

The above described method can be used to detect any nucleic acid sequence using known nucleic acid probes. Such nucleic acid sequences can be any nucleic acid sequences of DNA and RNA. In a preferred embodiment of the above method the nucleic acid sequence of interest is a DNA sequence and the probe is a DNA probe. In another preferred embodiment of the above method the nucleic acid sequence of interest is an RNA sequence and the probe is an RNA probe.

The following examples in the Experimental Details section is provided merely to illustrate the invention which is more fully defined in the claims which appear thereafter. The examples are not intended, and should not be interpreted, to limit the claims in any way.

First Series of Experiments

Experimental Methods

As merely a demonstration of the invention we have chosen to make antibody to the product of the reaction of peroxidase with 3,3'-diaminobenzidine (DAB). Once obtained, the antibody can then be labeled by any known method useful for detecting antibodies. Examples include labeling with peroxidase or other enzymes useful as labels for detection, or by labeling with biotin in which case the detection of the antibody of the subject invention takes place by known methods of avidin-enzyme or with avidin-fluorescein detection. The final signal can, therefore, be color, light or fluorescence.

EXAMPLE 1

Production of the antibody

A. Synthesis of antigen

Bovine serum albumin (BSA) (48 mg; 0.72 μmol) was dissolved in 2 mL of PBS and the pH adjusted to pH 6.5 with dilute sodium bicarbonate.

$DAB.4H_2O$ (7.6 mg; 21 μmol) was dissolved in 5 mL of PBS. Two microliters of 30% hydrogen peroxidase was added. To this solution was added 50 μL of a solution of 0.5 mg of peroxidase in 300 μL of distilled water. Color begins to appear immediately. When the color becomes bright red, a spatular tip of palladium black is immediately added, with mixing, to stop the reaction. The suspension was clarified by centrifugation and the supernatant added to the BSA solution. The pH was again adjusted to 6.5 and 40 μL of 25% glutaraldehyde added to the solution, which was allowed to stand at room temperature for 8 hours. Then 40 μL of ethanolamine was added and the solution to quench the glutaraldehyde and thereby stop the reaction. The solution was dialyzed overnight in a cold room.

B. Immunization with the antigen

Rabbits were immunized with this antigen in complete Freund's adjuvant hand boosted with antigen in incomplete adjuvant. Presence of specific antibody was determined by precipitation of a rabbit serum albumin (RSA) conjugate of the product, made by the above procedure, and by ELISA using the same RSA conjugate.

The specific antibody can be used as an antiserum or as a specifically purified antibody such as produced using immobilized RSA conjugate. In those cases, the antibody can be labeled by linking to peroxidase by standard procedures. Alternatively, the purified antibody can be biotinylated, and either avidin-peroxidase or avidin-fluorescein be used to produce a signal.

C. Purification of the antibody

The antibody need not be purified but can be used as antiserum. However, the antibody can be purified on an affinity column as follows.

The immunogen, in this case the RSA, conjugate of the partially polymerized 3,3'-diaminobenzidine, is immobilized by reaction with Affigel-10 (BIORAD) as described by the manufacturers of Affigel-10. The antiserum is incubated with the immobilized conjugate for 24 hour with mixing, at 4° C. After a thorough washing with PBS, the affinity purified antibody is eluted with 0.2M glycine—HCl, pH 2.5, and then quickly neutralized with Tris buffer pH 7.4. This is followed by dialysis against PBS for 2.0 hours.

The antibody is characterized by ELISA against the immunizing conjugate and by precipitation as described above.

EXAMPLE 2

Western and dot blot procedures for mouse proteins using amplification method

After application or transfer to a nitrocellulose membrane and blocking with 2% bovine serum albumin, the membrane is incubated at room temperature in phosphate buffered saline (PBS) containing 0.1% Tween-20 with a suitable dilution of goat anti-mouse antibody labeled with peroxidase for 30 minutes. The membrane is then washed with the above PBS-Tween solution and developed with 3,3'-diaminobenzidine (6 mg of 3,3'-diaminobenzidine in 10 mL of 5.0 mM Tris—HCl, pH 7.4 containing 10 microliters of 30% $H_2O_2$) 10 minutes at room temperature.

The membrane is then washed with PBS-Tween and incubated with the anti-product antibody of the subject invention at a suitable dilution, usually 1:500 dilution of the antiserum in PBS-Tween, at room temperature for 30 minutes.

The membrane is then washed and incubated with goat anti-rabbit Ig-peroxidase labeled at a dilution of 1:1000 dilution in PBS-Tween for 30 minutes. After another wash with PBS-Tween it is developed as before with 3,3'-diaminobenzidine.

EXAMPLE 3
Comparison of Detection methods
A. Dot Blot

FIGS. 1A–1D demonstrate the improved amplification provided by the claimed method over standard immunoassays and PAP-amplified immunoassays used to detect Cyclosporine A (CsA).

Four concentrations of Cyclosporine A-4-benzoylbenzoic acid-Bovine serum albumin conjugate (CsA-BBa-BSA) were applied to each of four strips of nitrocellulose membrane as a dot. From left to right on each membrane the concentrations are 500 ng, 100 ng, 20 ng, 4 ng, all in phosphate-buffered saline, pH 7.4 (PBS).

Figures 1A, 1B, 1C, 1D:
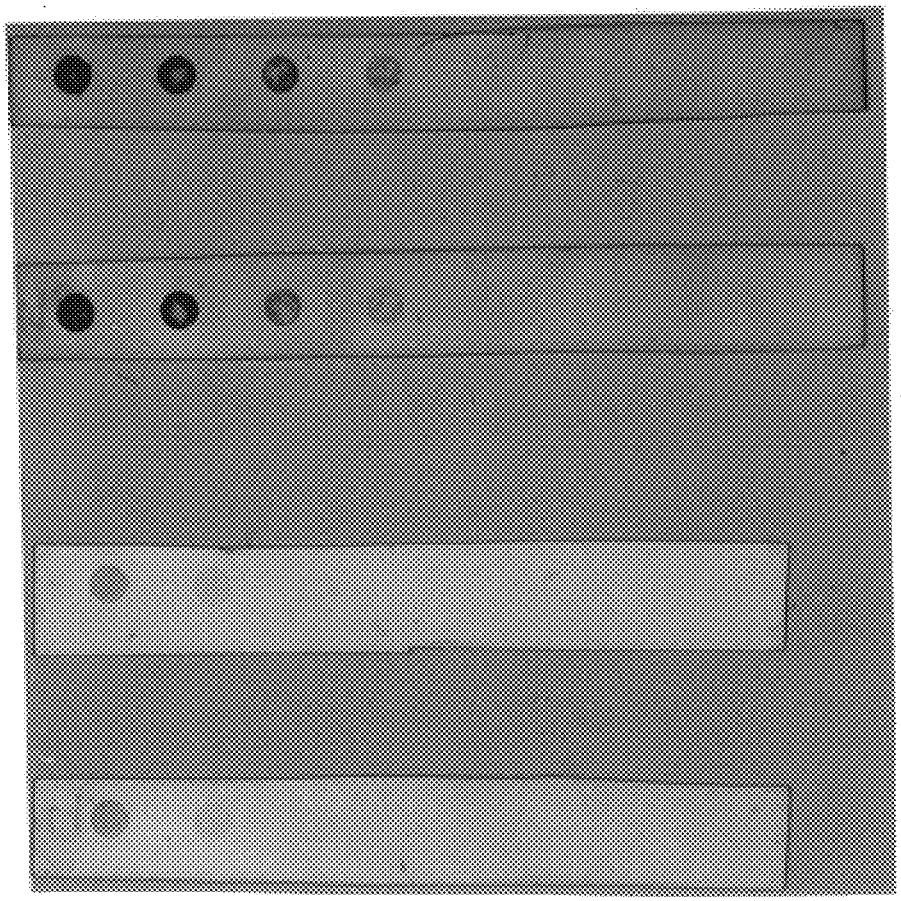
FIGS. 1A–1D: Nitrocellulose dot blot showing detection of Cyclosporine A-4-benzoyldibenzoic acid-BSA conjugate (CsA-BBA-BSA) applied to the nitrocellulose membrane (viewing left to right) in amounts of 500 ng, 100 ng, 20 ng, and 4 ng.

1. Standard Immunoassay. Membrane is incubated for 1 hour with 1 mg/mL of monoclonal mouse anti-cyclosporine antibody H4.13 for one hour. Excess is washed with PBS-0.1% Tween-20. Membranes are then incubated at room temperature with peroxidase labeled goat anti-mouse IgG for 30 minutes and excess labeled antibody removed with PBS-0.1% Tween-20. Membranes are then incubated with 10 mL of a solution of 6 mg 3,3'-diaminobenzidine, and 10 mL of 30% $H_2O_2$ in 50 mM Trishydroxyaminomethane pH 7.5 for about 10 minutes. FIG. 1A demonstrates that this procedure allows for the detection of concentrations of 500 ng and 100 ng only.

2. PAP Amplification. The method detailed above in A is repeated with the exception that after the incubation with goat anti-mouse antibody-peroxidase labeled, the membrane is incubated with peroxidase-anti-peroxidase antibody (PAP) according to known methods. FIG. 1B demonstrates that there is negligible amplification over the standard immunoassay shown in FIG. 1A.

3. Claimed Amplification Method. Again the method of A was repeated with the exception that after development with 3,3'-diaminobenzidine, the claimed anti-product antibody (R594) is incubated for 30 minutes with the dot blot. The antibody can be used as a biotinylated, specifically purified antibody (FIG. 1C) or 1:500 dilution of R594 antiserum (FIG. 1D). When using the purified labeled antibody, the membrane is developed using avidin-peroxidase and 3,3'-diaminobenzidine according to known procedures. When using the unpurified antibody, the membrane is developed by incubation with goat anti-rabbit peroxidase labeled antibody and then development with 3,3'-diaminobenzidine. FIGS. 1C and 1D demonstrate a 25-fold amplification over the standard immunoassay and PAP amplified assays showing detection of the 4 ng concentration sample.

B. Western blot.

Mouse immunoglobulin G was electrophoresed in an SDS-polyacrylamide gel according to known procedures.

FIG. 2A shows development of the Western blot with goat-anti-mouse IgG antibody peroxidase labeled and developed with 3,3'-diaminobenzidine according to the conditions outlined above for Standard Immunoassay techniques.

FIG. 2B shows detection with 1:500 dilution of R595 (anti-product antibody) anti-serum followed by peroxidase-labeled goat anti-rabbit antibody. Development was with 3,3'-diaminobenzidine according to the conditions outlined above for the claimed method. FIG. 2B demonstrates a 25-fold amplification of detection using the claimed method when compared to normal methods of detection in Western blot techniques.

EXAMPLE 4
Detection of nucleic acid molecules using amplification method

A sample of DNA is linearized by boiling a 100 mg/mL solution in 10 mM Tris—1 mM EDTA, pH 8 for 10 minutes, followed by quick-chilling on ice. For each 10 microliters of DNA solution, 1.1 µL of Psoralen-biotin reagent (Schelercher and Schuell) is added. The mixture is then irradiated at 365 nm for one hour. The cross-linked sample is then extracted twice with butanol to remove excess reagent and applied to a nitrocellulose membrane. The membrane is blocked with 2% bovine serum albumin. The sample on the membrane is then treated with a 1:1000 dilution of avidin-peroxidase and then visualized as in Example 2.

EXAMPLE 5
Comparison of DNA detection methods

A DNA sample was prepared as in Example 4 and applied to 2 nitrocellulose membranes at concentrations of 2.5 ng, 0.5 ng and 0.1 ng for each membrane. FIG. 3A shows development by standard immunoassay techniques with avidin-peroxidase, followed by the substrate 3,3'-diaminobenzidine. FIG. 3B shows development with the claimed method using the unpurified R595 antiserum followed by detection with peroxidase labeled goat anti-rabbit antibody and diaminobenzidine as discussed above. As demonstrated in FIGS. 3A and 3B, the claimed method provides for a 25-fold amplification, showing detection of the 0.5 ng and 0.1 ng DNA samples not seen with standard techniques.

Second Series of Experiments

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

Introduction

Enzyme-labeled antibodies are in common use in clinical and research laboratories for immunoassays and for identification of cell or tissue components. With respect to the latter, identification is usually performed by Western blotting after solubilization and electrophoresis, or by immunohistochemical procedures. In both cases, the signal for the presence of the target antigen is a deposit of a pigmented product of an enzyme-substrate reaction at the site of the antigen. The most common enzymes in use are alkaline phosphatase and horseradish peroxidase.

There are circumstances that require the signal to be amplified. These include the presence of low levels of the target antigen and/or limited availability or high cost of the target-specific antibody. Some representative amplification procedures are described in a review (Avrameas, 1992). Amplification of the signal produced by peroxidase is usually accomplished through the use of peroxidase-labeled anti-peroxidase antibody (PAP), biotin-avidin-peroxidase techniques, or the linking of primary antibodies to multiple enzyme molecules via polyvalent polymers (e.g. EPOS reagents: Dako, Carpinteria, Calif.), procedures that can produce significant amplification (Sternberger, 1986; Landsdorp et al., 1984; Sternberger, 1970). Other strategies have been reported to produce enhanced amplification, some of which have been applied to immunohistochemical systems. Among them are methods that exploit enzyme and co-factor cascades (Zaidi et al., 1990; Kemeny et al., 1989; Johansson et al. 1985; Blake et al., 1984). In another strategy, called catalyzed reporter deposition (CARD), substrates are designed to deposit a tagged product capable of producing an amplifiable signal, e.g., a biotinylated product that can be labeled with multiple avidin-enzyme conjugate (Bobrow et al., 1989, 1991, 1992).

A novel strategy is reported here, applicable to immunohistochemistry, which, in principle, is capable of exponential amplification of a peroxidase signal. It makes use of an antibody to the end-product of the action of peroxidase on 3,3'-diaminobenzidine (DAB). Because a single enzyme molecule converts many substrate molecules into product, a procedure that recognized molecules of product rather than molecules of enzyme should produce amplification of considerable magnitude.

Material and Methods

1. Preparation of Antigen and Specific Anti-End-product (Anti-EP) Antibody

Bovine serum albumin (BSA) (48 mg; 0.72 μmoles) was dissolved in 2 ml of PBS and the pH adjusted to 6.5 with dilute $NaHCO_3$. DAB 4HCL (7.6 mg; 21 μmoles) was dissolved in 5 ml of PBS. Two μl of 30% hydrogen peroxide was added. To this solution was added 50 μl of a solution of 0.5 mg of horseradish peroxidase in 300 μl of distilled water. Color began to appear immediately. When the solution became bright red, a spatular tip of palladium on carbon (10%) (Eastman; Rochester, N.Y.) was added immediately, with mixing, to stop the reaction. The suspension was centrifuged and the supernatant added to the BSA solution. The pH was again adjusted to 6.5 and 40 μl of 25% glutaraldehyde was added to the solution, which was allowed to stand at room temperature (RT) for 8 hr. Then 40 μl of ethanolamine was added to destroy the remaining glutaraldehyde and the solution was dialyzed overnight against PBS in a cold room. The conjugate was red-brown in color.

A rabbit serum albumin (RSA) conjugate was prepared in an identical way. Rabbits were immunized with the BSA conjugate in complete Freund's adjuvant and boosted several times with the antigen in incomplete Freund's adjuvant.

The presence of specific antibody was monitored by Ouchterloney and by ELISA using the RSA conjugate as the antigen, as follows.

Polystyrene 96-well microplated (Corning 25855) were coated with 100 μl of RSA conjugate (1 μl/ml in 0/1M sodium bicarbonate, pH 9.3) overnight at 4° C. The plates were washed three times with PBS containing 0.1% Tween 20 (PBS-T) and 100 μl of various dilutions of the antisera in PBS-T containing 1% horse serum were incubated in the wells at 37° C. for 2 hr. This was followed by three washes with PBS-T. Then a 1:1000 dilution of peroxidase-labeled goat anti-rabbit IgG (Sigma; St. Louis, Mo.) was added to each well. After a 1-hr incubation at 37° C. and three washes with PBS-T, development was carried out with 100 μl of substrate (7 mg of o-phenyl-enediamine dihydrochloride in 10 ml of 0.1M cirtate-phosphate buffer, pH 4.8, containing 5 μl of 30% $H_2O_2$). The reaction was stopped after 10 min by addition of 50 μl of 8N $H_2SO_4$, and the absorbance was read at 490 nm using a Dynatech Microplate reader. The results, shown in FIG. 1, indicated high titers of specific antibody, dilutions of 1:15,000 giving reproducible data.

Experiments

A panel of monoclonal and polyclonal primary antibodies was used (see Table 1 for sources of antibodies). Immunostaining was performed on formalin-fixed paraffin-embedded tissues obtained from the Surgical Pathology filed of the College of Physicians and Surgeons, Columbia University. Markers for B-(anti-CD 20 and anti-CD45RA) and T-(anti-CD3 and anti-CD 45RO) lymphocytes and macrophages (anti-CD68) were applied to tonsil tissue, in which the distribution of t-(interfollicular zones) and B-cells (germinal centers and mantle zones) is known. Also examined were five cases of Hodgkin's disease, in which an additional marker (anti-CD 30) that labels Hodgkin's cells and Reed-Sternberg cells was used. Immunolabeling for infectious agents was performed on cases of cerebral toxoplasmosis, progressive multifocal leukoencephalopathy (JC virus), and cytomegalovirus (CMV) pneumonia. The dilutions of primary antibodies for optimal staining, defined as maximal sensitivity of detection with and without the anti-EP amplification system in the absence of background staining, are listed in Table 1. Optimal staining without amplification, as determined by serial dilution experiments was in agreement with the manufacturer's recommendations.

The tissue sections were first treated with 1.5% hydrogen peroxide to quench endogenous peroxidase activity. For CD30 detection, antigen retrieval was accomplished by boiling for 20 min in 1.2 liters of 0.01M citrate buffer, pH 6.0 in a microwave oven: 15-min pepsin digestion (0.01 g/dl at pH 1.5) was used for CMV and CD68. Nonspecific staining was minimized by 20-min blocking with 10% horse serum in PBS for the monoclonal antibodies or 10% goat serum in PBS for the polyclonal antisera.

Sections were incubated with serial twofold dilutions of primary antibody for 1 hr at RT. followed by biotinylated second antibody: development was with a biotin-streptavidin-peroxidase kit (Vector Laboratories; Burlingame, Calif.) (Hsu et al. 1981). Peroxidase activity was visualized with DAB (250 μgml in PBS, form a stock solution of 1.25 g/50 ml of diethylene glycol) for 3–5 min. The sections were then rinsed throughly with tapwater for 30 min to remove unpolymerized DAB (Sigma) and blocked again with 10% goat serum in PBS for 20 min.

Amplification with anti-EP was accomplished by incubation one set of slides with 1:500 dilution of the anti-EP in PBS containing 3% goat serum for 30 min at RT, followed by biotinylated goat anti-rabbit IgG. To control for possible signal enhancement by the secondary anti-rabbit IgG, unamplified controls were run in which anti-EP was omitted. Apart from the omission of anti-EP, unamplified controls were treated exactly the same as EP-amplified sections. Development was with the Vector Laboratories biotin-avidin-peroxidase kit, which includes a biotinylated goat anti-rabbit antibody. DAB was applied for 1–2 min to demonstrate anti-EP binding and the degree of anti-EP amplification. The latter was determined by calculating the ratios of primary dilutions showing equal sensitivity of detection in anti-EP amplified sections and unamplified controls. In another set of experiments, designed to give an anti-EP amplified fluorescent signal, slides with and without application if anti-FP were developed with a biotin-streptavidin-alkaline phosphatase kit, which was visualized with Vector Red (Vector Laboratories).

Appropriate negative controls, in which nonspecific mouse and rabbit antibodies were substituted for specific primary antibodies gave negligible background.

Results

The signal amplification strategy reported in this article makes use of an antibody (anti-EP) raised in rabbits to a BSA conjugate of a polymeric intermediate formed by a controlled reaction of horse radish peroxidase and $H_2O_2$ on the substrate DAB. Amplification is the result of the ability of anti-EP to detect the multiplicity of product molecules formed by the action of a single molecule of enzyme on DAB.

Shown in FIG. 1 is the titer of anti-EP as determined by an ELISA in which a 96-well plate was coated with a rabbit serum albumin (RSA) conjugate of the polymeric DAB product. Reproducible titers could be obtained at dilutions of antisera as high as 1:15,000 with a development time of only 10 min.

In immunohistochemical studies, the intensity of Immunolabeling was increased 8- to 16-fold over conventional detection systems by using anti-EP amplification (Table 1). FIG. 2 illustrates the striking difference in signal intensity and number of immunoreactive cells between EP-amplified sections (FIGS. 2A, 2C, 2E, and 2G) and unamplified controls (FIGS. 2B, 2F, and 2H), when equals dilutions of the primary Ab were applied. The profile of immunoreactivity with respect to cell type remained unchanged before and after EP amplification for each Ab tested.

Anti-CD30 immunoreactivity was still confined to Reed-Sternberg cells in cases of Hodgkin's disease (FIGS. 2A and 2B). Anti-CD20 (FIGS. 2C and 2D) and anti-CD68 (FIGS. 2E and 2F) specifically labeled B-lymphocytes and macrophages, respectively, in germinal centers of hyperplastic tonsils. Immunoreactivity for CMV occurred only in cells displaying the characteristic pathomorphologic changes of CMV infection (FIGS. 2G and 2H). Nonspecific labeling of cells lacking the respective epitopes (CD20, CD30, CD68, or CMV) did not occur.

The specificity of anti-EP amplification was also tested by using a fluorescence end-point (Vector Red) for detection of anti-Ep immunoreactivity. Slides stained with antibodies to CD30 (FIGS. 3A–3D) and to toxoplasma (FIGS. 3E–3H) showed complete congruence between the DAB signal, representing the distribution of the primary antibodies, and the red fluorescence that represents anti-EP binding (FIGS. 3A, 3B, 3E, and 3F), demonstrating high specificity of the anti-EP labeling process. The fluorescence signal was absent (FIGS. 3C and 3G), despite a strong DAB signal (FIGS. 3d and 3h), when anti-EP Ab was omitted. This is further evidence that, in the unamplified controls, binding of biotinylated secondary goat anti-rabbit antibody to the primary antibodies did not occur.

Discussion

A procedure capable of an 8- to 16-fold amplification of a signal produced by the action on a substrate of an enzyme-linked antibody has been demonstrated (Table 1). Further optimization should be possible, as is the possibility of gaining increased amplification by repeating the cycle. This process of amplification has been shown to produce minimal background and allows the recognition of antigenic markers present at low concentrations, making possible a significant reduction (85–90%) in the amount of primary antibody necessary to produce a positive signal, a major cost-saving advantage in laboratories that routinely perform immunohistochemical procedures. The enzyme chosen was horseradish peroxidase and the substrate DAB but, in principle, the methodology should be applicable to other enzyme-substrate systems and moreover, it is not limited to signals produced by immune recognition.

The anti-EP used in the experiments described here is an antiserum containing polyclonal antibodies. Similar results can be obtained with globulin fractions, specifically purified antibodies and with biotinylated anti-EP followed by avidin-peroxidase, In preliminary experiments, amplifications as high as 50 fold were obtained with specifically purified rabbit anti-EP. Monoclonal anti-EP antibodies have also been raised, which have the advantage of uniformity from batch to batch and availability in essentially unlimited quantities.

The strategy of end-product amplification has also been applied to alkaline phosphatase action on tetrazolium substrates, which will be described in a subsequent report as will the application of end-product amplification to membrane immunoassays.

TABLE 1

Dilutions with optimal sensitivity of detection for each AB with and without anti-EP amplifications

| | | | Dilution | | |
|---|---|---|---|---|---|
| Type | Clone (primary AB) (animal) | Source | Without anti-EP | With amplification | Amplification |
| CD3 | Polyclonal (rabbit) | DAKO (Carpinteria, CA) | 1:100 | 1:800 | 8 |
| CD20 | L26 (mouse) | DAKO | 1:200 | 1:3200 | 16 |
| CD30 | HRS-4 (MOUSE) | IMMUNOTECH (Westbrook, MA) | 1:50 | 1:800 | 16 |
| CD45RA | 4KB% (mouse) | DAKO | 1:50 | 1:400 | 8 |
| CD45RO | UCHL-1 (mouse) | DAKO | 1:5 | 1:400 | 8 |
| CD68 | KP-1 (mouse) | DAKO | 1:1000 | 1:80 | 16 |
| Toxoplasma | Polyclonal (rabbit) | Serotec | 1:1000 | 1:16000 | 16 |
| SV-40 | Polyclonal (rabbit) | Serotec (Oxford, UK) | 1:1000 | 1:16000 | 16 |
| CMV | CCH2 (mouse) | DAKO | 1:25 | 1:200 | 8 |

REFERENCES

Avrameas S. (1992) J. Immunol. Methods 150: 23–32.
Blake D. A., Skarstedt M. T., Schultz J. L., Wilson D. P. (1984) Clin. Chem. 30: 1452–1456
Bobrow M. N., Harris T. D., Shaughnessy K. J., Litt G. J. (1989) J. Immunol. Methods 125: 279–285
Bobrow M. N., Litt G. J., Shaughnessy K. J., Mayer P. C., Conlon J. (1992) J. Immunol. Methods 150: 145–149
Bobrow M. N., Shaughnessy K. J., Litt G. J. (1991) J. Immunol. Methods 137: 103–112
Hsu S. M., Raine L., Fanger H. (1981) Am. J. Clin. Pathol. 75: 734–738
Johansson A., Stanley C., Self C. H. (1985) Clin. Chim. Acta. 120: 251–258
Landsdrop, P. M., van der Kwast T. H., de Boer M., Zeijlemaker W. P. (1984) J. Histochem. Cytochem 32: 172–178
Sternberger L. A. (1986) Immunocytochemistry 3rd ed. New York, Wiley
Sternberger L. A., Hardy P. H. Jr., Cuculus J. J., Meyer H. G. (1970) J. Hisotchem. Cytochem 18: 315–333
Zaidi M., Seth R., Girgis S. I., Self C. H. (1990) Clin. Chim. Acta. 36: 1288–1294

What is claimed is:

1. A method of detecting an antigen of interest in a sample which comprises:
   a) contacting the sample suspected of containing the antigen with a first labeled antibody which specifically binds the antigen under appropriate conditions to form a complex comprising the first labeled antibody bound to the antigen;
   b) removing any labeled antibody not bound in the complex formed in (a);
   c) contacting the complex from (b) with a substrate under appropriate conditions to produce a product of a reaction between the substrate and the labeling substance of the first labeled antibody in the complex of (b);
   d) contacting the product produced in (c) with a second labeled antibody which specifically binds the product under appropriate conditions to permit the second labeled antibody to bind to the product;
   e) removing any second labeled antibody not bound to the product in (d); and
   f) detecting the bound second labeled antibody, thereby detecting the antigen of interest.

2. The method of claim 1, wherein the antigen is a polypeptide.

3. The method of claim 2, wherein the polypeptide is expressed by an infectious agent.

4. The method of claim 3, wherein the infectious agent is a virus.

5. The method of claim 4, wherein the virus antigen is a cytomegalovirus.

6. The method of claim 3, wherein the infectious agent is a bacterium.

7. The method of claim 3, wherein the infectious agent is a protozoa.

8. The method of claim 3, wherein the infectious agent is a microorganism.

9. The method of claim 8, wherein the microorganism is a mycoplasma.

10. The method of claim 2, wherein the polypeptide is a expressed by a fungus.

11. The method of claim 2, wherein the polypeptide is expressed by a parasite.

* * * * *